| United States Patent [19] | [11] | 4,220,721 |
| Emert et al. | [45] | Sep. 2, 1980 |

[54] METHOD FOR ENZYME REUTILIZATION

[75] Inventors: George H. Emert, Merriam; Paul J. Blotkamp, Olathe, both of Kans.

[73] Assignee: University of Arkansas Foundation, Fayetteville, Ark.

[21] Appl. No.: 33,772

[22] Filed: Apr. 27, 1979

[51] Int. Cl.² ............................................. C12P 7/10
[52] U.S. Cl. ..................................... 435/165; 435/99; 435/161; 435/162; 435/163; 435/209; 435/252; 435/813; 435/815
[58] Field of Search ............... 435/161, 162, 163, 165, 435/99, 252, 209, 815, 813

[56] References Cited

U.S. PATENT DOCUMENTS

| 3,398,055 | 8/1968 | Bruno | 435/209 |
| 3,764,475 | 10/1973 | Mandels et al. | 435/209 |
| 3,990,944 | 11/1976 | Gauss et al. | 435/165 |
| 3,990,945 | 11/1976 | Huff et al. | 435/99 |

Primary Examiner—Lionel M. Shapiro
Attorney, Agent, or Firm—Donald R. Cassady

[57] ABSTRACT

Cellulase, an enzyme useful in the saccharification of cellulose can be recycled by a process of selective adsorption on cellulose containing materials and readmitted to the reaction mixture in a batch, semi-continuous, or continuous simultaneous saccharification-fermentation process.

6 Claims, No Drawings

METHOD FOR ENZYME REUTILIZATION

BACKGROUND OF THE INVENTION

The reutilization of waste cellulose by saccharification to sugars and concurrent manufacture of single-cell protein and by saccharification-fermentation to alcohols, acids, and the like, has lead to a search for new, more active, and cheaper sources of the enzyme cellulase.

One of the methods being employed is to search for fungi and mutants of fungi which naturally produce high yields of the enzyme when grown on selected nutrient media.

Another method is to reuse enzyme that has already catalyzed one or more saccharification reactions by recycling the enzyme. A recent patent, U.S. Pat. No. 4,009,075, to Hoge, details a method of concurrently vacuum-distilling a saccharification fermentation reaction to recover volatile products, in this case, ethanol-water, at below the decomposition point for the enzyme and reusing the residual reaction solution containing the enzyme in subsequent saccharification-fermentation reactions. This last procedure is adaptable to the recycling of cellulase from a reaction which yields a volatile product capable of being removed from the reaction vessel at temperatures where the enzyme is stable, i.e., below 35° C. as for example the procedure of Gauss, et al. U.S. Pat. No. 3,990,944.

However, the energy necessary to vacuum distill the ethanol from the reaction mixture at a sufficiently low temperature not to degrade the enzymes is of sufficient magnitude that alternative methods must be sought to recycle the active enzyme system or a portion thereof.

It has previously been shown that cellulase is comprised of at least three major active components useful in the degradation of cellulose to glucose units. These components are for convenience, named cellobiohydrolase, endoglucanase, and $\beta$-flucosidase herein. Of these components, the cellobiohydrolase (E.C.3.2.1.91) is considered to be responsible for the hydrolysis of cellulose with concurrent production of cellobiose residues, endoglucanase (E.C.3.2.1.4) is responsible for cleavage of cellulose internally at random points with concurrent production of lower molecular weight oligosaccharides, and $\beta$-glucosidase (E.C.2.2.1.21) which, while not a cellulose degrading enzyme in the sense of the above materials, catalyzes the decomposition of cellobiose to glucose.

It has also been shown that pure cellulose, as for example, Avicel, will adsorb and bind to cellobiohydrolase and endoglucanase thereby concentrating them from aqueous mixtures.

SUMMARY OF THE DISCLOSURE

This invention pertains to a method for recycling and reusing cellulase components in the simultaneous saccharification-fermentation of waste cellulose-containing materials.

More particularly this invention relates to a method for recycling and reusing cellulase components in the simultaneous saccharification-fermentation of waste cellulose-containing materials which involves adsorption of at least two components of the cellulase enzyme system on a freshly prepared portion of waste cellulose material and using the enzyme-waste cellulose combination as a portion of the feed to a further simultaneous saccharification-fermentation reaction.

During saccharification of cellulose in the presence of the enzyme cellulase in aqueous suspension, the solid cellulose materials become liquefied and dissolve in water. Depending upon the crystallinity and susceptibility of the cellulose toward degradation, from about 20 to about 80% of the solids will disappear from the suspension. Of the three major components of the cellulase enzyme system, two, cellobiohydrolase and endoglucanase, bind to solid cellulose; and during degradation and liquefaction, are released into the aqueous solution. The third, $\beta$-glucosidase, does not bind to the cellulose and remains in the aqueous phase at all times. Thus, at or near completion of a saccharification reaction, the components of cellulase are in solution and available for an appropriate recovery method.

It has now been found that the cellulase components retain their activity and are also in solution after a simultaneous saccharification-fermentation reaction which causes degradation of the cellulose to ethanol. Moreover, the presence of ethanol does not inhibit the recovery of cellobiohydrolase and endoglucanase from the solution.

Further, it has been discovered that increasing the concentration of endoglucanase and cellobiohydrolase alone in a simultaneous saccharification-fermentation reaction can improve the rate and yield of ethanol recovery. During simultaneous saccharification-fermentation the enzymic catalyzed rate of degradation of cellulose is improved to a point that the glucose content of the product increases faster than the yeast can consume it by conversion to ethanol. Thus, by recovering and reusing the enzyme components adsorbable on cellulose, one cannot only conserve the enzyme components but also improve the yield and rate of recovery of ethanol from a subsequent simultaneous saccharification-fermentation reaction.

Adsorption is preferably accomplished by filtering the reaction mixture to remove the solids and then adsorbing the enzymes from the filtrate by passing the reaction solution through a loosely packed plug of a portion of cellulose-containing starting material which will be utilized for subsequent simultaneous saccharification-fermentation reactions.

This plug, containing the recovered endoglucanase and cellobiohydrolase can be combined with additional starting material including additional enzyme inoculum to make up the initial concentration of $\beta$-glucosidase and the whole subjected to saccharification-fermentation in the usual manner. Alternatively, enough fresh inoculum is added to make up the customary initial concentration of cellobiohydrolase and endoglucanase. This would provide a deficiency in $\beta$-glucosidase, the cellobiose hydrolyzing enzyme. The lack of $\beta$-glucosidase concentration does not significantly adversely affect the yield or rate of ethanol formation, although the commonly used yeasts which ferment glucose to ethanol, as for example *Saccharomyces cerevisiae, Candida brassicae,* and *Rhizopus javanicus,* do not significantly ferment cellobiose to ethanol.

As an additional procedure, the aqueous ethanol solution from which the endoglucanase and cellobiohydrolase has been removed can be filtered through a plug of an oligosaccharide of 6 or more glucose units in lactone form. The oligosaccharide lactone binds the $\beta$-glucosidase fraction which can also be added to the subsequent saccharification reaction. Alternatively, the $\beta$-glucosidase can be adsorbed on conconavalin A, a haemagglutinizing protein isolated from the jack bean. Conconavalin A is available from Pharmacia Fine Chemicals, Piscataway, N.J., 08854, as Con A and Con A sepharose.

DETAILED DESCRIPTION OF THE INVENTION

Waste materials containing cellulose which have previously been disclosed as potential sources for degradation to simple organic molecules with the concurrent manufacture of a protein useful in animal feed are also useful as adsorbants for an enzyme recycling process. Sources of this waste material include municipal waste, paper mill waste, saw mill waste, cotton gin waste, and the like. Of particular utility are waste paper and cardboard which can be pre-swelled or pulped and will form a loosely packed plug useful for filtration or for slurry adsorption and which contains sufficient surface sites for enzyme adsorption.

Alternatively, a purified cellulose product can be used as an adsorbent which is then added to the starting materials. Such a purified cellulose is sold by American Viscose Division, FMC Corporation, Newark, Del., under the trade name Avicel.

Upon completion of a simultaneous saccharification-fermentation reaction, that is, upon reaction to substantial equilibrium, the reaction medium contains unreacted cellulose, solid oligosaccharides, lignocellulosic materials, and other undefined solid degradation products as well as alcohol, nutrients, cellulase enzyme components, and yeasts and yeast cells.

Filtration to remove the solid materials is usually the first step in purification of the desired ethanol product. The filtrate is then subjected to a vacuum stripping operation to remove the ethanol. By the method of this invention the enzymes from the saccharification reaction are saved and recycled prior to ethanol stripping.

By the method of this invention, any cellulose-containing solid material with sufficient surface area to provide binding sites for the enzyme, is contacted with the enzyme-containing filtrate from a simultaneous saccharification-fermentation reaction which has been allowed to attain substantial equilibrium of reaction. The method of contacting can be by adding the cellulose solid to form a slurry and rapid filtration of the slurry to recover the enzyme-cellulose solid or by passing the enzyme-containing filtrate through a plug of loosely packed cellulose solid.

In order for the rapid binding necessary to this method to occur it has been determined that the contact must be made at about pH 5 and above an ionic strength of 0.05 M. At ionic strengths from 0.05 M to 0, the enzymes will not bind and elution occurs. At below about pH 4.8 the enzymes will not bind and elution occurs. However, since by the method of this invention, the enzymes are adsorbed on a substrate that they themselves can cause to be destroyed given appropriate reaction conditions and can thereby be released into the media, the method of this invention is further accomplished by combining the adsorbed enzyme-cellulose mixture with fresh feed cellulose in a subsequent simultaneous saccharification-fermentation reaction without elution.

At above pH 8 the endoglucanase activity is lost by denaturation of the protein. For this reason the absorption must occur at between about pH 5 and pH 8; preferably at between about pH 5 and about pH 7.

Since, as noted above, the enzyme components act rapidly to cause degradation and liquefaction of the cellulose adsorbent, a reaction which occurs at above about 30° C., it is desirable to perform the adsorption at temperatures at or below ambient room temperature to inhibit degradation of the cellulose adsorbent. Temperatures from about 5° C. to about 20° C. are preferred.

Upon completion of the saccharification-fermentation reaction, some solid materials will remain, these may include, unreacted cellulose and solid degradation products, lignocellulose materials, unreactive solid components of the starting waste material, and the like. Inasmuch as a portion of the cellulase will remain on this accumulation of unreactive products, yield of reclaimed cellulase is not theoretical and additional fresh enzyme must also be used. This requirement for additional enzyme depends upon the amount and character of the solids in the reaction mixture and can only be ascertained by assay of the recovered enzyme.

This method is used advantageously to increase the cellulose-hydrolysis-rate-determining enzymes by adding fresh inoculum to a standard $\beta$-glucosidase activity or the method can be used to economize on use of fresh inoculum to provide a standard endoglucanase or cellobiohydrolase level.

Cellulase inoculum useful for the present invention can be purchased commercially from Meiji Seika Kaisha Ltd. of Tokyo, Japan as Meicelase P or manufactured as a metabolite from the growth of *Trichoderma viride, Trichoderma koningii, Fusarium solani, Fusarium javanicum,* and the like. The manner of preparing the aqueous culture mass containing the cellulolytic enzyme complex is conventional, the cellulolytic microorganisms being cultivated in known manner in an aqueous nutrient medium in the presence of a cellulosic material in shake flasks or in submerged culture. Typical methods are shown in an article by Mandels & Weber, *Advances in Chemistry Series,* ACS 95, 39–414 (1969).

Preferably the aqueous culture mass or an aliquot thereof is employed directly in the cellulose saccharification process without further treatment, except to adjust the pH if that is necessary, as described by the method of Huff & Yata, U.S. Pat. No. 3,990,945.

As the alcohol-producing microorganism to be simultaneously used with the cellulase, there can be employed such microorganisms as, for example, *Saccharomyces cerevisiae* and *Rhizopus javanicus* which have heretofore been used for the conversion of glucose into ethanol.

The procedure for recycle of cellulase components is adaptable to batch operation as will be described more particularly in the specific example hereinbelow. Care must be taken in adsorption of the enzyme on cellulose and transfers must be made with reasonable haste since the enzyme components adsorbed will solubilize the cellulose rather quickly by their catalytic effect on hydrolysis. Once solubilization has occurred the enzyme although still adsorbed to the soluble oligosaccharides will be lost to the supernatant. The process can also be adapted for semi-continuous operation by use of countercurrent columnar adsorption wherein the saccharification-fermentation product after filtration is countercurrently forced through a concentrated slurry of a portion of the starting cellulose-containing material. In this technique it is important to limit the contact time to minimize the amount of saccharification allowed to occur in the transfer chamber. As described above, dissolution of the cellulose without complete degradation to glucose can occur in the adsorbent chamber which will remove sites for adsorbence of enzyme.

EXAMPLE I

To duplicate 1 liter flasks (labeled A and B) were added:

229 grams of an aqueous hydropulped pulp mill fines slurry containing 6% cellulose;

200 ml of a cellulase solution of the following assay:

Filter paper reducing sugar activity by the method of Mandels and Weber, "The Production of Cellulases" Advances in Chemistry Series, ACS 95, 391–414 $28.20 \times 10^{-3}$, $\beta$-glucosidase by the method of Emert, Purification and Characterization of Cellobiase from *Trichoderma viride*, University of Microfilms 74–12,343, Virginia Polytechnic Institute and State University 1973, Pp. 28–29, $106.60 \times 10^{-2}$, and protein by the method of Emert loc.cit. p.34, 4.50 mg/ml;

250 ml of a nutrient media consisting of the following ingredients per liter of solution:

$KH_2PO_4$ 2.2 g, $MgSO_4.7H_2O$ 0.5 g, KCl 1.7 g, K citrate monohydrate 4.0 g, citric acid monohydrate 0.8 g, $CaCl_2$ 0.25 g, urea 2.5 g, yeast extract 1.0 g, $FeSO_4.7H_2O$ 10 mg, $MnSO_4.H_2O$ 10 mg, $ZnSO_4.7H_2O$ 10 mg, $CuSO_4$ 1 mg;

21 ml of water; and 25 ml of a suspension of *Saccharomyces cerevisiae* ATCC 4132 with a cell count of $200-250 \times 10^6$ cells/ml which had previously been grown for 18 hours. The contents of the flasks were stirred at 150 r.p.m. and 40° C. for 72 hours.

During the above reaction, additional duplicate samples (229 g each) of the above-described pulp mill fines were soaked in a solution of 0.04 m acetate buffer at pH 5 for 5 minutes and filtered to remove at least the volume of liquid representing the buffer. The contents of flasks A and B were centrifuged and the supernatant liquid added to the buffered samples of pulp mill fines and allowed to sit for 15 minutes then filtered to remove at least the amount of liquid added. The resulting mixtures (labeled 3 and 4) and two control mixtures (labeled 1 and 2), each containing 229 g of pulp mill fines were treated in the following manner: To each were added 25 ml of the above-described nutrient medium, 200 ml of the cellulase solution described above, 25 g. of the yeast solution described above and enough water to make a total weight of 500 g. The mixtures were allowed to react at 40° C. and 150 r.p.m. for 168 hours. Glucose and ethanol concentrations and conversions were determined at 48, 72, 96, 144, and 168 hours.

| Flask | Sample | EtOH mg/ml | Glucose mg/ml | Percent Conversion |
|---|---|---|---|---|
| 1 | 48 hr | 17.80 | 0.33 | 52.76 |
|   | 72 | 18.51 | 0.31 | 54.86 |
|   | 96 | 18.51 | 0.59 | 54.86 |
|   | 144 | 19.00 | 0.15 | 56.32 |
|   | 168 | 21.20 | 0.14 | 62.84 |
| 2 | 48 | 15.92 | 0.36 | 47.19 |
|   | 72 | 17.27 | 0.30 | 51.19 |
|   | 96 | 18.46 | 0.30 | 54.72 |
|   | 144 | 19.51 | 1.29 | 57.83 |
|   | 168 | 21.02 | 0.14 | 62.30 |

Samples 3 and 4 which had been allowed to contact the supernatant liquid obtained from the prior reaction demonstrated increased ethanol yield and conversion rate at up to 168 hours of reaction time.

We claim:

1. A method of recycling the endoglucanase (E.C.3.2.1.4) and cellobiohydrolase (E.C.3.2.1.91) portions of activity of cellulase enzyme which had been used as the cellulose hydrolyzing enzyme in a simultaneous saccharification-fermentation reaction of cellulose-to-ethanol by:

(1) separating the liquid fraction from the reaction mixture;
   (2) contacting this enzyme and alcohol-containing liquid fraction with a cellulose-containing solid which is useful for the simultaneous saccharification-fermentation reaction at between about pH 5 to about pH 8 and at above an ionic strength of 0.05 M to adsorb the enzymes thereupon;
   (3) separating the solid fraction containing the adsorbed enzymes; and
   (4) using the solid enzyme-cellulose combination as a portion of the feed to a further simultaneous saccharification-fermentation reaction.

2. The process of claim 1 wherein the enzyme and alcohol-containing liquid fraction and the cellulose-containing solid are contacted at between about 5° and about 20° C.

3. The process of claim 1 wherein the enzyme and alcohol-containing liquid fraction and the cellulose-containing solid are contacted by adding the solid to the liquid to form a slurry.

4. The process of claim 1 wherein the enzyme and alcohol-containing liquid fraction and the cellulose-containing solid are contacted by pouring the liquid through a loosely packed plug of the solid.

5. A series of simultaneous saccharification-fermentation reactions to manufacture ethanol from cellulose which comprises carrying out one simultaneous saccharification-fermentation reaction to substantial reaction equilibrium, separating the liquid fraction therefrom, contacting the liquid fraction with cellulose useful for a subsequent simultaneous saccharification-fermentation reaction at between about pH 5 to about pH 8 and above an ionic strength of 0.05 M to adsorb the endoglucanase (E.C.3.2.1.4) and cellobiohydrolase (E.C.3.2.1.91) portions of cellulase activity therefrom, separating the solid fraction, adding the solid fraction to a subsequent simultaneous saccharification-fermentation reaction and adding fresh cellulase inoculum to make up the cellobiohydrolase and endoglucanase to the standard level.

6. A series of simultaneous saccharification-fermentation reactions to manufacture ethanol from cellulose which comprises carrying out one simultaneous saccharification-fermentation reaction to substantial reaction equilibrium, separating the liquid fraction therefrom, contacting the liquid fraction with cellulose useful for a subsequent simultaneous saccharification-fermentation reaction at between about pH 5 to about pH 8 and above an ionic strength of 0.05 M to adsorb the endoglucanase (E.C.3.2.1.4) and cellobiohydrolase (E.C.3.2.1.91) portions of cellulase activity therefrom, separating the solid fraction, adding the solid fraction to a subsequent simultaneous saccharification-fermentation reaction and adding fresh cellulase inoculum to make up the $\beta$-glucosidase (E.C.3.2.1.21) enzyme activity to the standard level.

\* \* \* \* \*